United States Patent [19]

MacLeod

[11] Patent Number: 5,612,362
[45] Date of Patent: Mar. 18, 1997

[54] IMIDAZOLINONE DERIVATIVES AS TACHYKININ RECEPTOR ANTAGONISTS

[75] Inventor: Angus M. MacLeod, Bishops Stortford, United Kingdom

[73] Assignee: Merck Sharp & Dohme Ltd., Hoddesdon, England

[21] Appl. No.: 411,616

[22] PCT Filed: Oct. 14, 1993

[86] PCT No.: PCT/GB93/02131

§ 371 Date: Apr. 18, 1995

§ 102(e) Date: Apr. 18, 1995

[87] PCT Pub. No.: WO94/10168

PCT Pub. Date: May 11, 1994

[30]  Foreign Application Priority Data

Oct. 23, 1992 [GB] United Kingdom ............... 9222262

[51] Int. Cl.$^6$ .................. A61K 31/415; C07D 403/06
[52] U.S. Cl. .................. 514/392; 544/139; 546/201; 546/274.4; 548/311.4; 548/312.1; 514/235.2; 514/323
[58] Field of Search ............... 548/311.4, 312.1; 514/392

[56]  References Cited

FOREIGN PATENT DOCUMENTS 0545478  6/1993  European Pat. Off. .

OTHER PUBLICATIONS

Kazlauskas, R, et al. Tetrahedron Letters 1 (1977) 61–64.

Primary Examiner—Robert W. Ramsuer
Attorney, Agent, or Firm—Robert J. North; Melvin Winokur

[57]  ABSTRACT

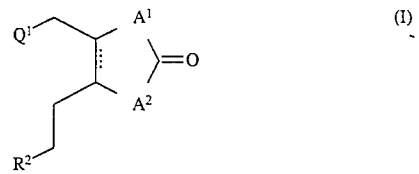

Compounds of formula (I) and salts and prodrugs wherein $Q^1$ is a specified aryl group, the dotted line is an optional double bond, Z is O or $NR^3$, $R^1$ and $R^3$ are H or specified optionally substituted alkyl or other substituents and $R^2$ is an optionally substituted phenyl or group are tachykinin receptor antagonists useful in medicine.

12 Claims, No Drawings

IMIDAZOLINONE DERIVATIVES AS TACHYKININ RECEPTOR ANTAGONISTS

This application is a 371 of PCT/GB93/02131, filed Oct. 14, 1993.

This invention relates to a class of heterocyclic compounds, in particular imidazolinone and oxazolinone derivatives, which are useful as tachykinin receptor antagonists.

The tachykinins are a group of naturally-occurring peptides found widely distributed throughout mammalian tissues, both within the central nervous system and in the peripheral nervous and circulatory systems. The three known mammalian tachykinins are: substance P, neurokinin A and neurokinin B:

Evidence for the usefulness of tachykinin receptor antagonists in pain, headache, especially migraine, Alzheimer's disease, multiple sclerosis, attenuation of morphine withdrawal, cardivascular changes, oedema, such as oedema caused by thermal injury, chronic inflammatory diseases such as rheumatoid arthritis, asthma/bronchial hyperreactivity and other respiratory diseases including allergic rhinitus, inflammatory diseases of the gut including ulcerative colitis and Crohn disease, ocular injury and ocular inflammatory diseases, proliferative vitreoretinopathy, irritable bowel syndrome and disorders of bladder function including cystitis and bladder detruser hyperreflexia is reviewed in "Tachykinin Receptors and Tachykinin Receptor Antagonists", C. A. Maggi, R Patacchini, P. Rovero and A. Giachetti, J. Auton. Pharmacol. (1993) 13, 23–93. Tachykinin antagonists are also believed to be useful in allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9], and as anticonvulsants [Garant et al., Brain Research (1986) 382 372–8]. Tachykinin antagonists may also be useful in the treatment of small cell carcinomas, in particular small cell lung cancer (SCLC) [Langdon et al., Cancer Research (1992) 52, 4554–7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), conjuctivitis, vernal conjunctivitis, contact dermatitis, atropic dermatitis, urticaria, and other eczematoid dermatitis (European patent application no. 0 394 989) and emesis (European patent application no. 0 533 280).

We have now found a class of non-peptides which are potent antagonists of tachykinins.

The present invention provides a compound of formula (I), or a salt or prodrug thereof:

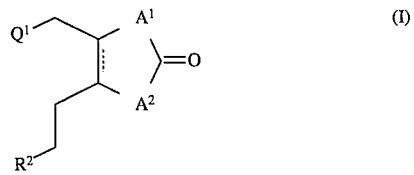

wherein $Q^1$ represents a phenyl group substituted by one or more halo, optionally substituted naphthyl, optionally substituted indolyl, optionally substituted benzthiophenyl, optionally substituted benzofuranyl, optionally substituted benzyl or optionally substituted fluorenyl;

the dotted line represents an optional covalent bond;

one of $A^1$ and $A^2$ represents $NR^1$ and the other is Z where Z represents O or $NR^3$;

$R^1$ and $R^3$ each independently represent H; $C_{1-6}$ alkyl optionally substituted by hydroxy, cyano, $COR^c$, $CO_2R^c$, $CONR^cR^d$, or $NR^cR^d$ (where $R^c$ and $R^d$ each independently represent H, $C_{1-6}$alkyl or $C_{0-4}$alkylphenyl optionally substituted in the phenyl ring by one or more of $C_{1-6}$alkyl, $C_{1-6}$alkoxy, halo or trifluoromethylmethyl); phenyl($C_{1-4}$alkyl) (optionally substituted in the phenyl ring by one or more of $C_{1-6}$alkyl, $C_{1-6}$alkoxy, halo and trifluoromethyl); $COR^c$; $CO_2R^c$; $CONR^cR^d$; $COC_{1-4}$alkyl$NR^cR^d$; $CONR^cCOOR^d$; $SO_2R^c$, where $R^c$ and $R^d$ are as above defined; $WR^6$ or $CO-Y-W-R^6$ where $R^6$ is an optionally substituted aromatic or non-aromatic azacyclic or azabicyclic group, Y is a bond, O, S or $NR^y$, where $R^y$ is H or $C_{1-6}$alkyl, and W represents a bond or a saturated or unsaturated hydrocarbon chain of 1, 2, 3, 4, 5 or 6 carbon atoms;

$R^2$ represents phenyl optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl.

For the avoidance of doubt, when the covalent bond represented by the dotted line is present, the compounds of formula (I) contain an olefinic double bond.

Aptly, this invention provides a compound of the formula (I) or a pharmaceutically acceptable salt thereof.

As used herein, the definition of each expression, when it occurs more than once in any structure, is intended to be independent of its definition elsewhere in the same structure.

The alkyl, alkenyl and alkynyl groups referred to with respect to any of the above formulae may represent straight, branched or cyclic groups or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

Where $Q^1$ represents optionally substituted fluorenyl, the group is linked through the bridgehead carbon atom, that is to say, C-9.

Where $Q^1$ represents optionally substituted naphthyl, indolyl, benzothiophenyl, benzofuranyl, benzyl or fluorenyl, suitable substituents include $C_{1-6}$ alkyl, $C_{1-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as above defined. One or more substituents may be present and each may be located at any available ring position, except, where $Q^1$ is optionally substituted indolyl, the nitrogen atom. Where $Q^1$ is optionally substituted indolyl, suitable nitrogen substituents include $C_{1-6}$alkyl, optionally substituted phenyl($C_{1-4}$alkyl), $COOR^a$ or $CONR^aR^b$, wherein $R^a$ and $R^b$ are as above defined.

Suitable values of the group $Q^1$ include 3,4-dichlorophenyl, 3-indolyl, 2-naphthyl, 3-naphthyl, 9-fluorenyl, benzyl, 3-benzothiophenyl and 3-benzofuranyl.

Preferably $Q^1$ is 3-indolyl, 3-benzothiophenyl or 3,4-dichlorophenyl, more preferably 3-indolyl.

The aromatic or non-aromatic azacycle or azabicycle $R^6$ may contain one or more additional heteroatoms selected from O and S, or groups $NR^7$, where $R^7$ is H or $C_{1-6}$alkyl, and may be unsubstituted or substituted. Suitable substituents include $C_{1-6}$alkyl, $C_{1-6}$alkoxy, oxo, SH, =S, halo, trifluoromethyl, $NR^aR^b$, $NR^aCOR^b$, $CONR^aR^b$, $CO_2R^a$ and $CH_2OR^a$, where $R^a$ and $R^b$ are as previously defined.

When $R^6$ represents an aromatic azacycle or azabicycle, suitable values of $R^6$ include imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl and indolyl, preferably imidazolyl, such as 2,4-imidazolyl, or pyridyl such as 4-, 3- or 2-pyridyl.

When $R^6$ represents a non-aromatic azacycle or azabicycle, suitable values of $R^6$ include morpholinyl, piperdinyl, pyrrolidinyl, piperazinyl, methylpiperazinyl, azanorbornanyl, 3,4-pyridinecarboxamido, quinuclidinyl, and azabicyclo[3.2.2]nonyl, preferably morpholinyl, piperazinyl, methylpiperazinyl, piperidinyl, pyrrolidinyl, quinuclidinyl (azabicyclo[2.2.2]octanyl) or azabicyclo[3.2.2]nonyl.

A subgroup of compounds according to the invention is represented by compounds of formula (I) wherein $R^1$ and $R^3$ each independently represent H; $C_{1-6}$alkyl optionally substituted by hydroxy, cyano, $COR^c$, $CO_2R^c$, $CONR^cR^d$, or $NR^cR^d$ (where $R^c$ and $R^d$ are as previously defined); phenyl($C_{1-4}$alkyl) (optionally substituted in the phenyl ring by one or more of $C_{1-6}$alkyl, $C_{1-6}$alkoxy, halo and trifluoromethyl); $COR^c$; $CO_2R^c$; $CONR^cR^d$; $COC_{1-4}$alkyl$NR^cR^d$; $CONR^cCOOR^d$; $SO_2R^c$; $(CH_2)_qR^6$ or $CO(CH_2)_qR^6$ where $R^6$ is as previously defined and q is 0, 1, 2, 3, 4, 5 or 6.

Preferably the double bond is present.

Aptly, $A^1$ represents O. In one group of particularly apt compounds $A^1$ is $NR^1$.

Preferably Z is $NR^3$.

In one group of compounds according to the invention, $R^3$ is preferably H or $C_{1-3}$alkyl, such as methyl.

In a preferred group of compounds of formula (I), $R^3$ represents $C_{1-6}$alkyl substituted by $NR^cR^d$ where $R^c$ and $R^d$ preferably represent $C_{1-6}$alkyl, such as $C_{1-4}$alkyl, e.g. methyl, or Y—W—$R^6$, where Y preferably represents a bond, W preferably represents a bond or $C_{1-4}$alkyl and $R^6$ is preferably pyridyl, especially 4-pyridyl, pyridinyl, such as 4-pyridinyl, or morpholinyl.

Preferably $R^1$ is H.

Preferably $R^2$ represents substituted phenyl. Suitable phenyl substituents include nitro, trifluoromethyl, trimethylsilyl, bromo, chloro, fluoro, iodo, cyano, methyl, ethyl, cyclopropyl, vinyl, methoxy, phenoxy and amino. Preferably $R^2$ represents monosubstituted or, more preferably, disubstituted phenyl wherein the substituents are selected from $C_{1-6}$alkyl, such as methyl, ethyl or t-butyl, $C_{1-6}$alkoxy, such as methoxy, halo such as bromo, chloro, fluoro or iodo, and trifluoromethyl. When $R^2$ represents monosubstituted phenyl, the substituent is preferably in the 3-position. When $R^2$ represents disubstituted phenyl, the substituents are preferably in the 3- and 5-positions.

Particularly preferred are compounds wherein $R^2$ represents 3,5-bis(trifluoromethyl)phenyl.

A particular subgroup of compounds according to the invention is represented by compounds of formula (Ia), and salts and prodrugs thereof:

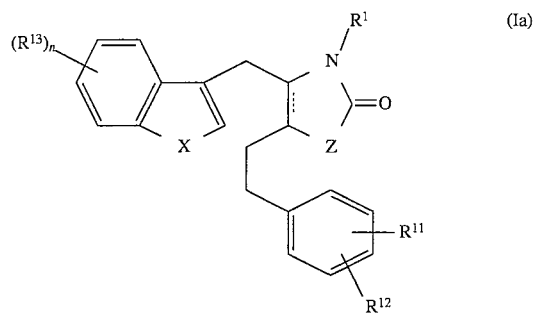

(Ia)

wherein the dotted line represents an optional covalent bond;

X represents O, S or $NR^{14}$ (where $R^{14}$ is H, $C_{1-6}$alkyl, optionally substituted phenyl($C_{1-4}$alkyl), $CO_2R^a$ or $CONR^aR^b$, where $R^a$ and $R^b$ are as previously defined), preferably S or NH;

Z is as defined for formula (I);

$R^1$ is as defined for formula (I), preferably H;

$R^{11}$ and $R^{12}$ each independently represent H, $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined;

each $R^{13}$ may occupy any available carbon atom of the bicyclic ring system and independently represents $C_{1-6}$alkyl, $C_2$-alkenyl, $C_2$-alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined; and n is 0, 1, 2 or 3, preferably 0.

Preferred are compounds of formula (Ia) wherein the optional covalent bond is present.

A further subgroup of compounds according to this invention are analogues of the compounds of the formula (Ia) but wherein $NR^1$ is replaced by O and Z is $NR^3$.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

The substance P antagonising activity of the compounds described herein was evaluated using the human NK1R assay described in published European patent application no. 0 528 495. The method essentially involves determining the concentration of the test compound required to reduce by 50% the amount of radiolabelled substance P binding to human NK1R, thereby affording an $IC_{50}$ value for the test compound. The compounds of the Examples were found to have $IC_{50}$ values of less than 500 nM.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

The invention further provides a process for the preparation of a pharmaceutical composition comprising a compound of formula (I), or a salt or prodrug thereof, and a pharmaceutically acceptable carrier, which process comprises bringing a compound of formula (I), or a salt or prodrug thereof into association with a pharmaceutically acceptable carrier.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotropic lateral sclerosis (ALS; Lou Gehrig's disease) and other neuropathological disorders such as peripheral neuropathy, for example, diabetic or chemotherapy-induced neuropathy, and postherpetic and other neuralgias; small cell carcinoma such as small cell lung cancer; respiratory diseases such as chronic obstructive airways disease, bronchopneumonia, bronchospasm and asthma; inflammatory diseases such as inflammatory bowel disease, irritable bowel syndrome, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like, and proliferative vitreoretinopathy; cutaneous diseases such as contact dermatitis, atropic dermatitis, urticaria, and other eczematoid dermatitis; oedema, such as oedema caused by thermal injury; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as cystitis and bladder detrusor hyperreflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis, post operative pain and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

Compounds of formula (I) wherein $A^2$ is $NR^3$, $R^3$ is other than H and the double bond is present, may be prepared from intermediates of formula (II):

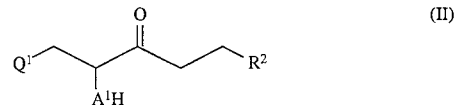

wherein $A^1$ is O or $NR^1$ and $Q^1$, $R^1$ and $R^2$ are as defined for formula (I), by reaction with an isocyanate of formula $R^3NCO$ where $R^3$ is as defined for formula (I), other than H, in the presence of a base.

Suitable bases of use in the reaction include organic bases, such as a tertiary amine, e.g. triethylamine, and inorganic bases, such as an alkali metal hydride, e.g. sodium hydride.

Compounds of formula (I) wherein $A^2$ is NH and the double bond is present may be prepared by reaction of an intermediate of formula (II) with an isocyanate of formula $R^{20}{}_3SiNCO$, where $R^{20}$ is alkyl, such as methyl, in the presence of a base, as previously described.

Compounds of formula (I) wherein Z is O and the double bond is present may be prepared by treatment of a compound of formula (III)

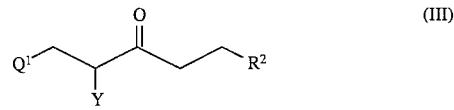

wherein $Q^1$ and $R^2$ are as defined for formula (I), and Y represents an activated carbamate, with a base, such as an alkali metal hydride, e.g. sodium hydride.

Suitably Y may represent an appropriately substituted aryl carbamate, e.g.

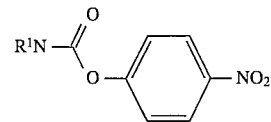

The reaction is conveniently effected in a suitable organic solvent, such as, for example, dimethyl formamide.

Compounds of formula (I) wherein the double bond is absent may be prepared from compounds of formula (IV)

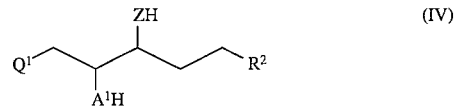

wherein $A^1$ is O or $NR^1$ and $Q^1$, Z, $R^1$ and $R^2$ are as defined for formula (I), by reaction with phosgene or a "phosgene equivalent" such as carbonyl diimidazole, a dialkyl carbonate or an alkylchloroformate, preferably with carbonyl diimidazole.

The reaction may be effected under basic conditions. Suitable bases include, for example, tertiary amines such as triethylamine.

The reaction is conveniently effected in a suitable organic solvent such as an ether, e.g. tretrahydrofuran, or a halogenated hydrocarbon, e.g. dichloromethane, suitably at room temperature.

Compounds of formula (I) may also be prepared from other compounds of formula (I). Thus, for example, compounds of formula (I) wherein the double bond is absent may in general be prepared from the corresponding compounds of formula (I) wherein the double bond is present, by reduction. Suitable reduction methods include, for example, hydrogenation in the presence of a catalyst, such as a nobel metal catalyst, e.g. palladium, which maybe supported, e.g. on carbon. Compounds of formula (I) wherein $R^1$ and/or $R^3$ is other than H may be prepared from compounds of formula (I) wherein R¹ and/or R³ represent H, by conventional procedures, for example alkylation.

Suitable alkylating agents and procedures will be readily apparent to those skilled in the art and include, but are not limited to, reaction with a suitable optionally substituted alkyl halide in the presence of a base, such as an alkali metal hydride, e.g. sodium hydride.

Compounds of formula (II) may be prepared from intermediates of formula (V):

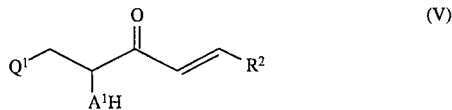

wherein $A^1$ is O or $NR^1$ and $Q^1$, $R^1$ and $R^2$ are as defined for formula (I), by reduction.

Suitable reduction procedures include catalytic hydrogenation. Suitable hydrogenation catalysts include nobel metals, for example, platinum or palladium, or oxides thereof, which may be supported, for example, on charcoal.

The reaction is conveniently effected in a suitable organic solvent, such as an ether, e.g. tetrahydrofuran, an alcohol, e.g. ethanol, or an ester, e.g. ethyl acetate, suitably at ambient temperature.

Intermediates of formula (V) may be prepared by reaction of an aldehyde of formula $R^2CHO$ with a compound of formula (VI):

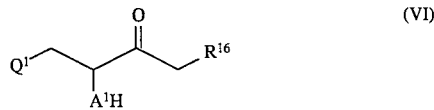

wherein $A^1$ is O or $NR^1$ and $Q^1$ and $R^1$ are as defined for formula (I) and $R^{16}$ represents a group $PR^x_3$ or $PO(OR^x)2$, wherein $R^x$ represents phenyl or $C_{1-10}$alkyl, in the presence of a base.

Suitable bases include alkali metal hydrides, such as, for example, sodium hydride, and strong organic bases such as, for example, 1,8-diazabicylo[5.4.0] undec-7-ene in the presence of anhydrous lithium chloride.

The reaction is conveniently effected in a suitable organic solvent, such as an ether, e.g. tetrahydrofuran, suitably at ambient temperature.

Compounds of formula (VI) may be prepared from compounds of formula (VII):

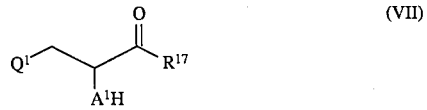

wherein $A^1$ is O or $NR^1$ and $Q^1$ and $R^1$ are as defined for formula (I) and $R^{17}$ represents an alkoxy or a suitably substituted amino group, such as a group $NR^yOR^z$, where $R^y$ and $R^z$ represent alkyl, in particular a group $NCH_3(OCH_3)$, by reaction with a compound of formula $CH_3PO(OR^x)_2$, where $R^x$ is an alkyl group, in the presence of a base.

Suitable reaction procedures will be readily apparent to the skilled person and examples thereof are described in the accompanying Examples.

Suitable bases of use in the reaction include alkyl lithiums, such as butyl lithiums.

Compounds of formula (VII) are commercially available or may be prepared using standard procedures well known to the person skilled in the art. The compounds of formula (VII) where $A^1$ is $NR^1$ are amino acid derivatives. Syntheses of amino acids and derivatives thereof are well documented and are described, for example, in *Chemistry and Biochemistry of the Amino Acids,* ed. G. C. Barrett, Chapman and Hall, 1985.

Compounds of formula (III) may be prepared from compounds of formula (II) by reaction with a suitable chloroformate, for example

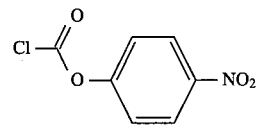

in the presence of a base, such as a tertiary amine, for example, triethylamine.

Compounds of formula (IV) wherein Z is O may be prepared from compounds of formula (II) by reduction. Suitable reducing agents include, for example, hydride reducing agents such as, for example, sodium borohydride.

Compounds of formula (IV) wherein Z is S may be prepared from the corresponding compounds of formula (IV) wherein Z is O by treatment with Lawesson's reagent or phosphorous pentasulphide in a suitable solvent, e.g. pyridine, at ambient or elevated temperature.

Where the above-described processes for the preparation of the compounds according to the invention give rise to mixtures of stereoisomers, these isomers may be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (–)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry,* ed. J. F. W. McOmie, Plenum Press, 1973; and T. W. Greene and P. G. M. Wuts, *Protective Groups in Organic Synthesis,* John Wiley & Sons, 1991. The protecting groups may be removed at a convenient subsequent stage using methods known from the art.

Using the methods described in PCT/GB92/01212 (International Publication No. WO 93/01159), pages 30–33, it was found that the compounds of the Examples referred to hereinafter had $IC_{50}$ at NKIR of less than 500 nM.

The following non-limiting Examples illustrate the preparation of compounds according to the invention.

EXAMPLE 1

1-Methyl-4-(indol-3-ylmethyl)-5-(3,5-bis(trifluoromethyl)phenethyl)imidazolin-2-one (a) N-Methoxy-N-methyl 2-t-butyloxycarbonylamino-3-(3-indolyl)propionamide N-α-BOC-L-tryptophan (100 g) was dissolved in dimethyl formamide (800 ml) and triethylamine (101 g) was added. The reaction was cooled to −30° C. and isobutyl chloroformate (42.5 ml) was added, maintaining the internal temperature to below −20° C. The reaction was stirred for 15 minutes before adding N,O-dimethyl hydroxylamine hydrochloride (64 g) and then diluting the reaction with dichloromethane (1 l), maintaining the internal temperature below 0° C. The reaction was stirred for 15 minutes, poured into ethyl acetate (3l) and washed with 10% citric acid (1 l), water (3×1 l), saturated sodium bicarbonate (1 l) and water (1 l). The organic phase was dried ($MgSO_4$), filtered, and evaporated until crystallisation ensued. The suspension was diluted with petroleum ether, filtered and dried to yield the title compound; mp 129°–130° C.; $^1$H NMR (360MHz, $D_6$ DMSO) δ 10.80 (1H, s); 7.51 (1H, d, J=7Hz); 7.33 (1H, d, J=7Hz); 7.16 (1H, s); 7.08–6.97 (3H, m); 4.62–4.58 (1H, m); 3.72 (3H, s); 3.34 (3H, s); 3.02–2.81 (2H, m); 1.31 (9H, s).

(b) 2-t-Butyloxycarbonyl amino-1-(3-indolyl)-4-dimethylphosphono-3-butanone

Dimethyl methane phosphonate (205 g) was dissolved in tetrahydrofuran (800 ml), cooled to −70° C.; and then treated with n-butyllithium (1.6M in hexane, 900 ml), maintaining the internal temperature of the reaction at below −55° C. The reaction was stirred for one hour before adding the product of part (a) (90 g). The reaction was stirred at −70° C. for 30 minutes before quenching with saturated ammonium chloride. The resulting mixture was extracted with ethyl acetate and the organic extract was washed with water (5×500 ml), dried ($MgSO_4$) and evaporated. The residue was purified on silica (eluting with ethyl acetate) to yield the title compound as an oil; $^1$H NMR (360MHz, $CDCl_3$) δ 10.84 (1H, s), 7.56 (1H, d, J=7Hz), 7.33 (1H, d, J=7Hz), 6.98 (1H, t, J=7Hz), 4.34–4.31 (1H, m), 3.63 (6H, d, J=11Hz), 3.39 (2H, d, J=22Hz), 3.19–3.11 (1H, m), 2.91–2.84 (1H, m); found: C, 55.73, H, 6.34; N, 6.80; $C_{19}H_{27}N_2O_6P$ requires C, 55.60; H, 6.63; N, 6.82%.

(c) 5-(3,5-Bis(trifluoromethyl)phenyl)-2-t-butyloxycarbonylamino-1-(3-indolyl)-4-penten-3-one A solution of the product of part (b) (69.0 g) in acetonitrile (600 ml) was stirred with diisopropylethylamine (43.3 g), and anhydrous lithium chloride (14.13 g) for 30 minutes before adding 3,5-bistrifluoromethylbenzaldehyde (55 g) in acetonitrile (200 ml). The reaction was stirred for two hours then the solvent was removed and the residue partitioned between ethyl acetate and water. The organic phase was washed with 10% citric acid (500 ml), water (500 ml), saturated sodium bicarbonate (500 ml) and water (500 ml). The solution was dried ($MgSO_4$), filtered and evaporated. The residue was purified by column chromatography on silica using ethyl acetate/petroleum ether (1:4) to yield the title compound as a pale yellow solid, mp 137°–138° C.; found: C, 59.23; H, 4.79; N, 5.35; $C_{26}H_{24}F_6N_2O_3$ requires C, 59.32; H, 4.60; N 5.32%.

(d) 5-(3,5-Bis(trifluoromethyl)phenyl)-2-t-butyloxycarbonylamino-1-(3-indolyl)-3-pentanone The product of part (c) was heated under reflux with tri-n-butyltin hydride (51.12 g) in toluene for 20 hours. The reaction was cooled and purified by column chromatography on silica using ethyl acetate/petroleum ether (1:4) to yield the title compound as a white solid (37.1 g), mp 138°–140° C.: found: C, 59.23; H,4.90; N, 5.28; $C_{26}H_{24}F_6N_2O_3$ requires C, 59.09, H, 4.96; N, 5.30%.

(e) 2-Amino-5-(3,5-bis(trifluoromethyl)phenyl)-1-(3-indolyl)-3-pentanone Hydrochloride The product of part (d) was treated with ethereal hydrogen chloride for one hour. The precipitated white solid was filtered and dried, mp 84°–86° C.; found: C, 54.40; H, 4.25; N, 6.10; $C_{21}H_{18}F_6N_2O \cdot HCl$ requires C, 54.26; H, 4.12; N, 6.03%.

(f) 1-Methyl-4-(indol-3-ylmethyl)-5-(3,5-bis(trifluoromethyl)phenethyl)imidazolin-2-one To a stirred suspension of the compound of part 1(e) (475 mg) in dichloromethane (15 ml) was added methyl isocyanate (0.15 ml) and triethylamine (0.5 ml). After 1.5 hours the reaction was washed with dilute hydrochloric acid, then aqueous sodium bicarbonate, dried ($Na_2SO_4$) and concentrated. Crystallisation from ethyl acetate/diethyl ether gave the title compound, mp 191° C.; Found: C, 58.07; H, 3.99; N, 8.84. $C_{23}H_{19}F_6N_3O \cdot 0.5H_2O$ requires C, 57.99; H, 4.23; N, 8.82.

EXAMPLE 2

4-(3,5-Bis(trifluoromethyl)phenethyl)-5-(indol-3-ylmethyl) imidazolin-2-one

Prepared by the method of Example 1(f) using trimethylsilylisocyanate and obtained as white crystals, mp 194°–195° C.; found: C, 57.66; H, 3.72; N, 9.16. $C_{22}H_{17}F_6N_3O \cdot 0.25H_2O$ requires C, 57.71; H, 3.85; N, 9.18.

EXAMPLE 3

4-(Indol-3-ylmethyl)-5-(3,5-bis(trifluoromethyl)phenethyl) oxazolin-2-one

(a) 2-(4-Nitrophenoxycarbonylamino)-5-(3,5-bis(trifluoromethyl)phenyl)-1-(3-indolyl)-3-pentanone The compound of Example 1(e) (1 g) in tetrahydrofuran (10 ml) was treated with bis-(4-nitrophenyl)carbonate (0.66 g) and triethylamine (0.3 ml). After stirring for 24 hours the reaction was diluted with ethyl acetate, washed with water, dried ($Na_2SO_4$) and concentrated. Crystallisation from ethyl acetate-petroleum ether gave the title compound as a white solid.

(b) 4-(Indol-3-ylmethyl)-5-(3,5-bis(trifluoromethyl)phenethyl) oxazolin-2-one A solution of the product of Example 3(a) (300 mg) in dimethylformamide (5 ml) was treated with sodium hydride (20 mg of a 60% dispersion in oil) for 16 hours. The reaction was diluted with ethyl acetate, washed with water, dried ($NaSO_4$) and concentrated. The residue was purified by chromatography on silica gel eluting with ethyl acetate-petroleum ether to give the title compound which was recrystallised from ethyl acetate-petroleum ether, mp 178°–180° C.; found: C, 58.01; H, 3.75; N, 6.11. $C_{22}H_{16}F_6N_2O_2$ requires C, 58.16; H, 3.55; N, 6.16.

EXAMPLE 4

4-(Indol-3-ylmethyl)-5-(3,5-bis(trifluoromethyl)phenethyl) oxazolidin-2-one (a) 5-(3,5-Bis(trifluoromethyl)phenyl)-2-t-butoxycarbonylamino-1-(1-t-butoxycarbonylindol-3-yl)-3-pentanone The product of Example 1(d) (6.7 g) in dichloromethane (200 ml) was treated with di-tertbutyl dicarbonate (2.75 g) and N,N-dimethylaminopyridine (1.5 g) for 2 hours. The reaction mixture was washed with aqueous citric acid, sodium bicarbonate solution and water then dried ($Na_2SO_4$) and concentrated to give an oil which was purified by chromatography on silica gel. A sample of the product thus obtained (2 g) was dissolved in methanol and treated with sodium borohydride (120 mg) for 1 hour. The solvent was evaporated and the residue partitioned between ethyl acetate and water. The organic solution was separated, dried and concentrated to give a residue which was purified by chromatography on silica to give the title compound as two separate diastereomers, isomer A and isomer B.

(b) 4-(Indol-3-ylmethyl)-5-(3,5-bis(trifluoromethyl)phenethyl) oxazolidin-2-one

The compound of Example 4(a), isomer A (70 mg), was dissolved in ethereal hydrogen chloride for 1 hour. The mixture was concentrated and the residue dissolved in dichloromethane (5 ml) to which was added triethylamine (0.5 ml) and carbonyl diimidazole (100 mg). After stirring for 1 hour the reaction was diluted with ethyl acetate, washed with dilute hydrochloric acid then sodium bicarbonate solution, dried and concentrated. Chromatography on silica gel eluting with ethyl acetate-petroleum ether (1:3) gave the title compound, isomer A, mp 196°–198° C.; found: C, 55.80; H, 4.02; N, 5.96. $C_{22}H_{20}F_6N_2O_3$ requires C, 55.70; H, 4.25; N, 5.91.

In a similar manner the compound of Example 4(a), isomer B, gave the title compound, isomer B.

EXAMPLE 5

1-Ethyl-4-(indol-3-ylmethyl)-5-(3,5-bis(trifluoromethyl) phenethyl)imidazolin-2-one To a stirred suspension of the compound of Example 1(e) (468 mg) in dichloromethane (15 ml) was added ethyl isocyanate (0.5 ml) and triethylamine (1 ml). After 1 hour the solution was washed with dilute hydrochloric acid, aqueous sodium bicarbonate, dried ($Na_2SO_4$) and concentrated. The residue was dissolved in methanol 5 ml and treated with sodium methoxide (0.4 g) for 1.5 hours after which time the solution was diluted with dichloromethane, washed with water, dried and concentrated. Crystallisation from diethyl ether gave the title compound, mp 228°–230° C.; found: C, 59.15; H, 4.42; N, 8.55. $C_{24}H_{21}F_6N_3O.0.25H_2O$ requires C, 59.32; H, 4.46; N, 8.65.

EXAMPLE 6

1-(4-Pyridylmethyl)-4-(indol-3-ylmethyl)-5-(3,5-bis(trifluoromethyl)phenethyl)imidazolin-2-one a) 5-(3,5-Bis(trifluoromethyl)phenyl)-1-(3-indolyl)-2-(4-pyridylmethylureido)-3-pentanone Hydrochloride The compound of Example 1(e) (400 mg) in tetrahydrofuran (10 ml) was treated with triethylamine (0.12 ml) and 4-nitrophenylchloroformate (174 mg) for 1 hour. The solvent was removed in vacuo and the residue partitioned between ethyl acetate and water. The organic solution was dried ($Na_2SO_4$) and concentrated to give a solid which was dissolved in tetrahydrofuran (15 ml). 4-Aminomethylpyridine (0.085 ml) was added and the solution stirred for 16 hours then concentrated in vacuo. The residue was partitioned between ethyl acetate and potassium carbonate solution. The organic solution was dried ($Na_2SO_4$), concentrated and the residue treated with ethereal hydrogen chloride to give the title compound, mp 171°–174° C.; found: C, 53.94; H, 4.31; N, 8.87%. $C_{27}H_{25}F_6N_4O_2.HCl.1.5H_2O$ requires C, 53.72; H, 4.50; N, 8.95%.

b) 1-(4-Pyridylmethyl)-4-(indol-3-ylmethyl)-5-(3.5-bis-(trifluoromethyl)phenethyl)imidazolin-2-one The compound of part 7(a) (0.1 g) in methanol (5 ml) was treated with sodium methoxide (225 mg) for 16 hours, then diluted with ethyl acetate, washed with water, dried and concentrated. Crystallisation of the residue from ethyl acetate-petroleum ether gave the title compound, mp 222°–224° C.; found: C, 61.61; H, 4.31; N, 10.07. $C_{28}H_{22}F_6N_4O$ requires C, 61.76; H, 4.07; N, 10.29.

EXAMPLE 7

1-Dimethylaminoethyl-4-(indol-3-ylmethyl)-5-(3,5-bis(trifluoromethyl)phenethyl)imidazolin-2-one Prepared by the method of Example 6 using 2-N,N-dimethylaminoethylamine. Mp 189°–191° C.; found: C, 58.73; H, 4.82; N, 10.40. $C_{26}H_{26}F_6N_4O.0.3H_2O$ requires C, 58.93; H, 5.05; N, 10.52.

EXAMPLE 8

1-Methyl-3-methyl-4-(indol-3-ylmethyl)-5-(3,5-bis(trifluoromethyl)phenethyl)imidazolin-2-one The compound of Example 1 (0.5 g) in tetrahydrofuran (5 ml) was treated with sodium hydride (43 mg of a 60% dispersion in oil) under a nitrogen atmosphere with stirring. After 5 minutes methyl iodide (0.28 g) was added and stirring continued for 2 hours. The reaction was diluted with ethyl acetate, washed with water, dried and concentrated. The residue was purified by chromatography on silica gel eluting with ethyl acetate-petroleum ether and crystallised from ethyl acetate-petroleum ether to give the title compound, mp 202°–205° C.; found: C, 59.88; H, 4.23; N, 8.42. $C_{24}H_{21}F_6N_3O$ requires C, 59.88; H, 4.40; N, 8.73.

EXAMPLE 9

1-Dimethylaminopropyl-4-(indol-3-ylmethyl)-5-(3,5-bis(trifluoromethyl)phenethyl)imidazolin-2-one Prepared by the method of Example 6 using 3-N,N-dimethylaminopropylamine. Mp. 209°–211° C.; found: C, 60.15; H, 5.30; N, 10.28. $C_{27}H_{28}F_6N_4O$ requires C, 60.22; H, 5.24; H, 10.40.

EXAMPLE 10

1-(4-Piperidinyl)-4-(indol-3-ylmethyl)-5-(3,5-bis(trifluoromethyl)phenethyl)imidazolin-2-one N-$^t$Butoxycarbonylisonipecotic acid (458 mg) in dichloromethane (10 ml) was treated with triethylamine (0.28 ml) and diphenylphosphoryl azide (0.43 ml) for 16 hours. The solvent was removed under reduced pressure and the residue redissolved in dichloromethane (15 ml) to which was added triethylamine (0.2 ml) and the compound of Example 1(e). After stirring for 6 hours the solvent was evaporated and the residue partitioned between water and ethyl acetate. The ethyl acetate solution was separated, dried ($Na_2SO_4$) and concentrated to give a residue which was purified by chromatography on silica gel eluting with ethyl acetate-petroleum ether (1:1). The resulting oil was dissolved in ethereal hydrogen chloride for 2 hours. The solution was washed with sodium bicarbonate solution, dried ($Na_2SO_4$) and evaporated to give the title compound, mp 190° C. (decomp.); found: C, 57.71; H, 4.78; N, 9.67. $C_{27}H_{26}F_6N_4O \cdot 1.5H_2O$ requires C, 57.55; H, 5.18; N, 9.94.

EXAMPLE 11

1-(2-(N-Morpholinyl)ethyl)-4-(indol-3-ylmethyl)-5-(3,5-bis(trifluoromethyl)phenethyl)imidazolin-2-one Prepared by the method of Example 6 using N-(aminoethyl) morpholine. Mp 207° C.; found: C, 59.52; H, 5.13; N, 9.60. $C_{28}H_{28}F_6N_4O_2$ requires C, 59.36; H, 4.98; N, 9.89.

EXAMPLE 12

1-(4-Piperidinylmethyl)-4-(indol-3-ylmethyl)-5-(3,5-bis(trifluoromethyl)phenethyl)imidazolin-2-one Hydrochloride The compound of Example 1(e) was treated with 4-nitrophenylchloroformate and N-Boc-4-aminomethylpiperidine (Synthetic Communications (1992), 22, 2357) by the method of Example 6. After the reaction had stirred for 16 hours dichloromethane was added and the solution washed with water, dried and concentrated. The residue was purified by chromatography on silica gel eluting with ethyl acetate-petroleum ether to give a solid which was dissolved in ethereal hydrogen chloride for 16 hours. The solvent was removed in vacuo and the residue crystallised from propan-2-ol/di-isopropyl ether to give the title compound, mp 250° C. (decomp.); found: C, 57.28; H, 4.63; N, 9.34. $C_{28}H_{28}F_6N_4O \cdot HCl$ requires C, 57.29; H, 4.98; N, 9.54.

EXAMPLE 13

4-(3,5-Bis(trifluoromethyl)phenethyl)-5-(indol-3-ylmethyl)-3-methyloxazolin-2-one (a) N-Methoxy-N-methyl-2-t-butyldimethylsilyloxy-3-(3-indolyl)propionamide Indole lactic acid (5.0 g) was suspended in dichloromethane (100 ml) and treated with triethylamine (6.8 ml) and t-butyldimethylsilyl triflate (5.7 ml) for 24 hours. iso-Butyl chloroformate (3.1 ml) was added followed by N,O-dimethylhydroxylamine (2.4 g) and triethylamine (3.4 ml). The solution was stirred for 24 hours then washed with water, dried ($Na_2SO_4$) and concentrated. The residue was purified by chromatography on silica gel eluting with ethyl acetate-petroleum ether to give the title compound as a white solid.

(b) 5-(3,5-Bis(trifluoromethyl)phenyl)-2-t-butyldimethylsilyloxy-1-(3-indolyl)-4-penten-3-one Prepared from the compound of Example 13(a) by the methods of Examples 1(b) and 1(c).

(c) 5-(3,5-Bis(trifluoromethyl)phenyl)-2-hydroxy-1-(3-indolyl)-3-pentanone

The compound of Example 13(b) in ethyl acetate was shaken under an atmosphere of hydrogen gas at 50 psi over 10% Pd—C for 24 hours. The mixture was filtered, concentrated and dissolved in tetrahydrofuran containing tetrabutylammonium fluoride for 3 hours. The solution was diluted with water and extracted with diethyl ether which was then dried and concentrated to give a residue which was purified on silica gel eluting with ethyl acetate-petroleum ether (2:3). Crystallisation from diethyl ether-petroleum ether gave the title compound as a white solid.

(d) 4-(3,5-Bis(trifluoromethyl)phenethyl)-5-(indol-3-ylmethyl)-3-methyloxazolin-2-one The compound of Example 13(c) (0.15 g) was dissolved in methyl isocyanate (1 ml). After 6 hours the solution was concentrated in vacuo and the residue dissolved in methanol (2 ml) containing sodium methoxide for 30 minutes. The solution was diluted with diethyl ether and washed with 5N hydrochloric acid, dried and concentrated. The residue was purified on silica gel eluting with ethyl acetate-hexane (2:3) to give the title compound as a white solid, mp 109°–110 ° C.; found: C, 59.22; H, 3.86; N, 5.70. $C_{23}H_{18}F_6N_2O_2$ requires C, 58.98; H, 3.87; N, 5.98.

The following examples illustrate pharmaceutical compositions according to the invention.

EXAMPLE 14A

Tablets Containing 1–25 mg of Compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 14B

Tablets Containing 26–100 mg of Compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 15

Parenteral Infection

|  | Amount mg |
| --- | --- |
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 16

Topical Formulation

|  | Amount mg |
| --- | --- |
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

I claim:

1. A compound of formula (I), or a salt or prodrug thereof:

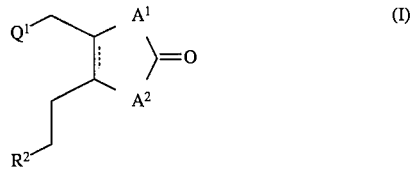

wherein $Q^1$ represents optionally substituted indolyl, optionally substituted benzthiophenyl, or optionally substituted benzofuranyl;

the dotted line represents an optional covalent bond;

one of $A^1$ and $A^2$ represents $NR^1$ and the other is $NR^3$;

$R^1$ and $R^3$ each independently represent H; $C_{1-6}$alkyl optionally substituted by hydroxy, cyano, $COR^c$, $CO_2R^c$, $CONR^cR^d$, or $NR^cR^d$ (where $R^c$ and $R^d$ each independently represent H, $C_{1-6}$alkyl or $C_{0-4}$alkylphenyl optionally substituted in the phenyl ring by one or more of $C_{1-6}$alkyl, $C_{1-6}$alkoxy, halo or trifluoromethylmethyl); phenyl ($C_{1-4}$alkyl) (optionally substituted in the phenyl ring by one or more of $C_{1-6}$alkyl, $C_{1-6}$alkoxy, halo and trifluoromethyl); $COR^c$; $CO_2R^c$; $CONR^cR^d$; $COC_{1-4}$alkyl$NR^cR^d$; $CONR^cCOOR^d$; $SO_2R^c$, where $R^c$ and $R^d$ are as above defined; $WR^6$ or $CO—Y—W—R^6$ where $R^6$ is an optionally substituted aromatic or non-aromatic azacyclic or azabicyclic group, Y is a bond, O, S or $NR^y$, where $R^y$ is H or $C_{1-6}$alkyl, and W represents a bond or a saturated or unsaturated hydrocarbon chain of 1, 2, 3, 4, 5 or 6 carbon atoms;

$R^2$ represents phenyl optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl.

2. A compound as claimed in claim 1 wherein $R^1$ and $R^3$ each independently represent H; $C_{1-6}$alkyl optionally substituted by hydroxy, cyano, $COR^c$, $CO_2R^c$, $CONR^cR^d$, or $NR^cR^d$; phenyl($C_{1-4}$alkyl) (optionally substituted in the phenyl ring by one or more of $C_{1-6}$alkyl, $C_{1-6}$alkoxy, halo and trifluoromethyl); $COR^c$; $CO_2R^c$; $CONR^cR^d$; $COC_{1-4}$alkyl$NR^cR^d$; $CONR^cCOOR^d$; $SO_2R^c$; $(CH_2)_qR^6$ or $CO(CH_2)_qR^6$ where q is 0, 1, 2, 3, 4, 5 or 6.

3. A compound of formula (I) or a pharmaceutically acceptable salt thereof as claimed in claim 1 wherein the double bond is present.

4. A compound as claimed in claim 1 wherein $R^3$ is H or $C_{1-3}$alkyl.

5. A compound as claimed in claim 1 wherein $R^3$ reprsents $C_{1-6}$alkyl substituted by $NR^cR^d$ or $Y—W—R^6$.

6. A compound as claimed in claim 1 wherein $R^2$ is phenyl substituted by one or more of $C_{1-6}$alkyl, $C_{1-6}$alkoxy, halo or trifluoromethyl.

7. A compound as claimed in claim 1 selected from:

1-methyl-4-(indol-3-ylmethyl)-5-(3,5-bis(trifluoromethyl)phenethyl)imidazolin-2-one;

4-(3,5-bis(trifluoromethyl)phenethyl)-5-(indol-3-ylmethyl)imidazolin-2-one;

1-ethyl-4-(indol-3-ylmethyl)-5-(3,5-bis(trifluoromethyl)phenethyl)imidazolin-2-one;

1-(4-pyridylmethyl-4-(indol-3-ylmethyl)-5-(3,5-bis(trifluoromethyl)phenethyl)imidazolin-2-one;

1-dimethylaminoethyl-4-(indol-3-ylmethyl)-5-(3,5-bis-(trifluoromethyl)phenethyl)imidazolin-2-one;

1-methyl-3-methyl-4-(indol-3-ylmethyl)-5-(3,5-bis(trifluoromethyl)phenethyl)imidazolin-2-one;

1-dimethylaminopropyl-4-(indol-3-ylmethyl)-5-(3,5-bis-(trifluoromethyl)phenethyl)imidazolin-2-one;

1-(4-piperidinyl)-4-(indol-3-ylmethyl)-5-(3,5-bis(trifluoromethyl)phenethyl)imidazolin-2-one;

1-(2-(N-morpholinyl)ethyl)-4-(indol-3-ylmethyl)-5-(3,5-bis(trifluoromethyl)phenethyl)imidazolin-2-one;

1-(4-piperidinylmethyl)-4-(indol-3-ylmethyl)-5-(3,5-bis-(trifluoromethyl)phenethyl)imidazolin-2-one hydrochloride;

and their pharmaceutically acceptable salts and prodrugs thereof.

8. A pharmaceutical composition comprising a compound as claimed in claim 1 in association with a pharmaceutically acceptable carrier.

9. A method for the treatment of a physiological disorder associated with an excess of tachykinins, which method comprises administration to a patient in need thereof of a tachykinin-reducing amount of a compound according to claim 1.

10. A method according to claim 9 for the treatment of pain or inflammation.

11. A method according to claim 9 for the treatment of migraine.

12. A method according to claim 9 for the treatment of arthritis.

\* \* \* \* \*